United States Patent [19]

Aichinger et al.

[11] Patent Number: 4,905,150
[45] Date of Patent: Feb. 27, 1990

[54] X-RAY DIAGNOSTICS INSTALLATION WITH MEAN PARENCHYMA DOSE CALCULATOR

[75] Inventors: Horst Aichinger, Fuerth; Karlheinz Koehler, Herzogenaurach, both of Fed. Rep. of Germany

[73] Assignee: Siemens Aktiengesellschaft, Berlin and Munich, Fed. Rep. of Germany

[21] Appl. No.: 261,084

[22] Filed: Oct. 24, 1988

[30] Foreign Application Priority Data

Jan. 18, 1988 [DE] Fed. Rep. of Germany ....... 3801210

[51] Int. Cl.$^4$ ..................... H05G 1/26; G06F 15/42
[52] U.S. Cl. ................................................ 364/413.26
[58] Field of Search ...................... 364/413.26, 413.16, 364/413.27; 378/901

[56] References Cited

U.S. PATENT DOCUMENTS

| | | | |
|---|---|---|---|
| 4,277,744 | 7/1981 | Andone et al. | 324/72 |
| 4,614,178 | 9/1986 | Harlt et al. | 128/24 A |
| 4,729,049 | 3/1988 | Iverson et al. | 364/413.26 |

FOREIGN PATENT DOCUMENTS

| | | |
|---|---|---|
| 0200272 | 11/1986 | European Pat. Off. |
| 0218367 | 4/1987 | European Pat. Off. |
| WO87/01555 | 3/1987 | PCT Int'l Appl. |

Primary Examiner—Jerry Smith
Assistant Examiner—Gail O. Hayes
Attorney, Agent, or Firm—Hill, Van Santen, Steadman & Simpson

[57] ABSTRACT

An x-ray diagnostics installation, of the type suitable for mammography, includes a calculator, such as a computer, which calculates the mean parenchyma dose based on a prescribed relationship from exposure values. The mean parenchyma dose can be read from the computer by a printer to obtain a permanent record.

3 Claims, 1 Drawing Sheet

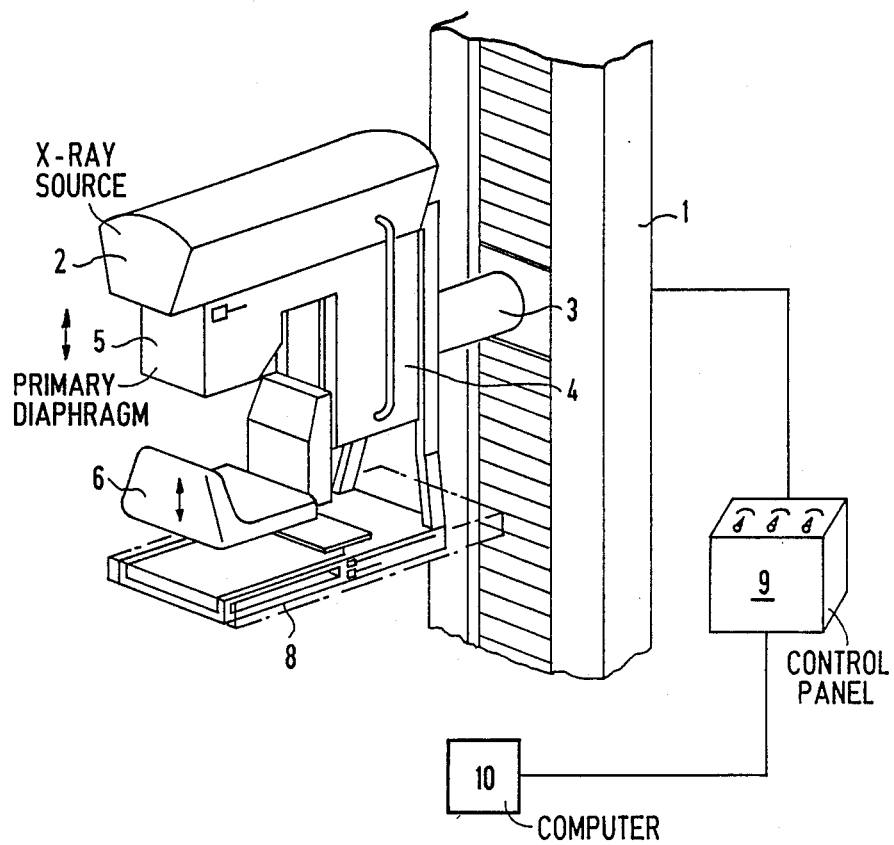

X-RAY DIAGNOSTICS INSTALLATION WITH MEAN PARENCHYMA DOSE CALCULATOR

BACKGROUND OF THE INVENTION

1. Field of the Invention

The present invention is directed to x-ray diagnostics installation, and in particular to such installations suitable for mammography exposures.

2. Description of the Prior Art

A knowledge of the amount of radiation to which a patient has been exposed in the production of an x-ray exposure is needed to estimate the radiation risk to the patient. In addition to being dependent upon known characteristics of a particular x-ray apparatus, the radiation exposure is dependent on data which may change from exposure to exposure, such as the tube voltage, the product of the tube current and the duration which the tube is energized by the automatic exposure unit, and the attenuation of any filter which may be used. The radiation exposure is also dependent upon the sensitivity of the imaging system (film-foil system) and on the thickness of the subject. The dose quantity relevant for estimating the radiation risk is the mean parenchyma dose. Given a known sensitivity of the imaging system, and an exit radiation dose defined as a result thereof, the mean parenchyma dose can be calculated by measuring the entry dose. It is not usually possible, however, to undertake a simultaneous measurement of the x-ray dose with the production of an x-ray exposure of a patient. It is known, however, to calibrate an x-ray installation using a phantom, which is equivalent to the tissue to be examined, so that an estimate of the mean parenchyma dose can be undertaken by measuring the product of the tube current and the duration of the exposure time.

SUMMARY OF THE INVENTION

It is an object of the present invention to provide an x-ray diagnostics installation for mammography exposures wherein an automatic calculation of the mean parenchyma dose can be undertaken without the intervention of attending personnel.

The above object is achieved in accordance with the principles of the present invention in an x-ray diagnostics installation having a computer to which electrical signals corresponding to the respective exposure values are supplied, and which calculates the mean parenchyma dose from those values based on a specific equation, described in detail below.

The mean parenchyma dose, calculated by the computer, can be generated as an output signal by the computer via a printer so that a permanent record can be maintained. The calculation is possible because all dose-relevant data required for the calculation are provided in digital form after the exposure has been completed. Certain calibration factors required for the calculation of the entry dose can be stored in the memory of the computer.

DESCRIPTION OF THE DRAWINGS

The single FIGURE is a perspective view of an x-ray diagnostics installation constructed in accordance with the principles of the present invention, with electrical components being schematically shown in block diagram form.

DESCRIPTION OF THE PREFERRED EMBODIMENTS

An x-ray diagnostics installation constructed in accordance with the principles of the present invention is shown in the drawing. The installation includes a stand 1 to which an x-ray source 2 is connected in a height-adjustable manner by a shaft 3 disposed perpendicularly to a central ray of the x-ray source 2. The shaft 3 carries the x-ray source 2 via a mounting block 4, on which a primary radiation diaphragm 5 is also arranged. The mounting block 4 additionally carries a compression plate 6 which is motor-adjustable in the direction of the central ray of the x-ray source 2. An exposure table 8 is provided for support of the examination subject. The examination subject is compressed on the exposure table with the compression plate 6, and an x-ray exposure on an x-ray film cassette, inserted into the exposure table 8, is obtained.

Feed and control of the x-ray diagnostics installation is achieved by a control panel 9, which permits exposure values to be manually set. The control panel is connected to a computer 10, which includes a memory, to which electrical signals corresponding to the entered exposure values, as well as other operating values, are supplied. The computer 10 calculates the mean parenchyma dose $\overline{D}$ from those values according to the following equation:

$$\overline{D} = \frac{f \cdot J_E}{a \cdot (d - 2d_F)} \cdot [e^{-a \cdot d_F} - e^{-a(d - d_F)}]$$

wherein
f = 1.03 (conversion factor),
d = subject thickness in cm,
$d_F$ = thickness of the fatty tissue, with $d_F = 0.5$ cm for $d \leq 5.0$ cm and $d_F = 1.0$ cm for $d > 5.0$ cm,
$J_E = k \cdot (I \cdot t)$, wherein
I = x-ray tube current,
t = exposure time, and
k = calibration factor, and
$a = 1/d \cdot \ln J_E/J_A$, wherein
$J_A$ = exit dose.

The calibration of the x-ray diagnostics installation can be undertaken using phantoms of various thicknesses consisting of, for example, plexiglas, in accordance with the following table:

| Tube Voltage | Subject Thickness | Equivalent Tissue Thickness | Entry Dose | Exit Dose | K-Factor |
|---|---|---|---|---|---|
| 28 kV | 3 cm | 3 cm | Gy | Gy | Gy/mA |
| 30 kV | 4 cm | 3.1–5 cm | Gy | Gy | Gy/mA |
| 32 kV | 5 cm | 3.1–7 cm | Gy | Gy | Gy/mA |
| 34 kV | 6 cm | 7 cm | Gy | Gy | Gy/mA |

The exit dose is determined by the film-foil system which is used, and is selected such that a mean blackening of 1.5 is achieved at the film.

A correction of the calculated entry dose can be unertaken according to the following equations for various exposure techniques:

$$J_{Ecorr} = J_E \cdot \frac{(60 - d_p)^2}{(60 - d)}$$

$$J_{Ecorr} = J_E \cdot \frac{(33.9 - d_p)^2}{(33.9 - d)}$$

wherein d is, as above, the subject thickness in cm, and $d_p$ is the phantom thickness in cm.

Although modifications and changes may be suggested by those skilled in the art it is the invention of the inventors to embody within the patent warranted hereon all changes and modifications as reasonably and properly come within the scope of their contribution to the art.

We claim as our invention:

1. An x-ray diagnostics installation for mammography exposures comprising:

means for generating an x-ray beam in which an examination subject is disposed;

means for recording an x-ray image formed by radiation attenuated by said examination subject; and means for calculating a means parenchyma dose $\overline{D}$ for said examination subject according to the following equations:

$$D = \frac{f \cdot J_E}{a \cdot (d - 2d_F)} \cdot [e^{-a \cdot d_F} - e^{-a(d - d_F)}]$$

with f = 1.03 (conversion factor)
d = subject thickness in cm
$d_F$ = thickness of the fatty tissue
$d_F$ = 0.5 cm for d ≦ 5.0 cm
$d_F$ = 1.0 cm for d ≦ 5.0 cm
$J_E = k \cdot (I \cdot t)$
I = x-ray tube current
t = exposure time
k = calibration
$a = 1/d \cdot \ln J_E/J_A$
$J_A$ = exit dose.

2. An x-ray diagnostics installation as claimed in claim 1 for use in a scan technique of said examination subject, wherein said means for calculating further includes means for calculating a corrected entry dose $JE_{corr}$ using a phantom having a thickness $d_p$ in cm according to the following equation:

$$J_{Ecorr} = J_E \cdot (60 - d_p)^2 / (60 - d).$$

3. An x-ray diagnostics installation as claimed in claim 1 for use in an enlargement technique of said x-ray exposure wherein said means calculating includes means for calculating a corrected entry dose $J_{Ecorr}$ using a phantom having a thickness $d_p$ in cm according to the following equation:

$$J_{Ecorr} = J_E \cdot (33.9 - d_p)^2 / (33.9 - d).$$

* * * * *